(12) United States Patent
Kim et al.

(10) Patent No.: US 9,157,428 B2
(45) Date of Patent: Oct. 13, 2015

(54) MICRO-PUMP

(71) Applicant: SAMSUNG ELECTRO-MECHANICS CO., LTD., Suwon, Gyunggi-do (KR)

(72) Inventors: Sang Jin Kim, Gyunggi-do (KR); Bo Sung Ku, Gyunggi-do (KR)

(73) Assignee: Samsung Electro-Mechanics Co., Ltd., Suwon-si (KR)

( * ) Notice: Subject to any disclaimer, the term of this patent is extended or adjusted under 35 U.S.C. 154(b) by 296 days.

(21) Appl. No.: 13/779,368

(22) Filed: Feb. 27, 2013

(65) Prior Publication Data

US 2014/0134715 A1 May 15, 2014

(30) Foreign Application Priority Data

Nov. 12, 2012 (KR) .................. 10-2012-0127216

(51) Int. Cl.
*F04B 43/04* (2006.01)
*F04B 53/10* (2006.01)
*B01L 3/00* (2006.01)
*C12M 1/00* (2006.01)

(52) U.S. Cl.
CPC ........... *F04B 43/046* (2013.01); *B01L 3/50273* (2013.01); *C12M 29/00* (2013.01); *F04B 43/043* (2013.01); *F04B 53/1067* (2013.01); *B01L 2400/0439* (2013.01); *B01L 2400/0481* (2013.01); *B01L 2400/0605* (2013.01); *B01L 2400/0616* (2013.01)

(58) Field of Classification Search
CPC .. F04B 43/043; F04B 43/046; F04B 53/1067; F04B 53/107; F04B 53/106; C12M 29/00

USPC ............................................ 417/413.2, 413.3
See application file for complete search history.

(56) References Cited

U.S. PATENT DOCUMENTS

| | | | |
|---|---|---|---|
| 5,718,567 A * | 2/1998 | Rapp et al. ................... | 417/395 |
| 2004/0052657 A1* | 3/2004 | Van Lintel et al. ........... | 417/322 |
| 2004/0120836 A1* | 6/2004 | Dai et al. .................... | 417/413.2 |
| 2006/0140782 A1* | 6/2006 | Weber ........................ | 417/221 |
| 2006/0245951 A1* | 11/2006 | Ball, Jr. ...................... | 417/413.3 |
| 2009/0232680 A1* | 9/2009 | Kitahara et al. ............ | 417/413.2 |
| 2011/0103980 A1* | 5/2011 | Mandica .................... | 417/413.2 |

FOREIGN PATENT DOCUMENTS

| | | |
|---|---|---|
| JP | 2000-249074 A | 9/2000 |
| JP | 2004-092588 A | 3/2004 |
| KR | 2008-0070358 A | 7/2008 |

OTHER PUBLICATIONS

Office Action issued on Jan. 24, 2014 in the corresponding Korean patent application No. 10-2012-0127216.

* cited by examiner

*Primary Examiner* — Charles Freay
*Assistant Examiner* — Kenneth J Hansen
(74) *Attorney, Agent, or Firm* — NSIP Law (57) ABSTRACT

There is provided a micro-pump including: a bottom substrate; a flow path forming substrate coupled to the bottom substrate and including an inlet having a fluid introduced therein and an outlet having the fluid ejected therefrom; and a valve substrate coupled to the flow path forming substrate and including at least one valve controlling the fluid to be introduced and ejected.

16 Claims, 7 Drawing Sheets

MICRO-PUMP

CROSS-REFERENCE TO RELATED APPLICATIONS

This application claims the priority of Korean Patent Application No. 10-2012-0127216 filed on Nov. 12, 2012, in the Korean Intellectual Property Office, the disclosure of which is incorporated herein by reference.

BACKGROUND OF THE INVENTION

1. Field of the Invention

The present invention relates to a micro-pump, and more particularly, to a micro-pump capable of uniformly supplying a small amount of fluid.

2. Description of the Related Art

Observation of a reaction between new drugs and a cell is required for developing new drugs and testing the stability thereof. In general, a reaction test between a drug and a cell is performed by using a culture dish, or the like.

However, since a reaction between a drug and a cell, occurring in the culture dish, is significantly different from a reaction between the drug and the cell, occurring inside a body, it may be difficult to accurately observe or examine a reaction between a drug and a cell only through a result of the test using the culture dish. Therefore, development of a new device that can observe the reaction between the drug and the cell in a similar environment to that of a body is required.

To this end, the applicant has developed a technology of circulating a culture medium. However, since a small amount of culture medium needs to be constantly supplied, for smoothly culturing the cell, the development of a micro-pump for uniformly supplying a small amount of fluid is needed.

Meanwhile, there are Patent Documents 1 and 2 as prior art inventions relating to micro-pumps. According to Patent Documents 1 and 2, a small amount of fluid may be moved by using driving force of a piezoelectric element. However, Patent Document 1 does not include a valve that completely blocks a fluid flow, which makes it difficult to transfer a quantitative amount of fluid. Unlike this, Patent Document 2 includes valves 5 and 6 provided in valve substrates 3 and 4, respectively, which makes it possible to transfer the quantitative amount of fluid; however, it is disadvantageously difficult to manufacture the valve substrates 3 and 4.

RELATED ART DOCUMENT (Patent Document 1) KR No. 2008-070358 A
(Patent Document 2) JP No. 2000-249074 A

SUMMARY OF THE INVENTION

An aspect of the present invention provides a micro-pump capable of uniformly supplying a small amount of fluid.

According to an aspect of the present invention, there is provided a micro-pump including: a bottom substrate; a flow path forming substrate coupled to the bottom substrate and including an inlet having a fluid introduced therein and an outlet having the fluid ejected therefrom; and a valve substrate coupled to the flow path forming substrate and including at least one valve controlling the fluid to be introduced and ejected.

The inlet and outlet may be formed in a first surface of the flow path forming substrate, and a pressure chamber connecting the inlet and the outlet to each other may be formed in a second surface of the flow path forming substrate.

The micro-pump may further include: an actuator formed on the first surface of the flow path forming substrate and applying pressure to the pressure chamber.

The bottom substrate and the flow path forming substrate may be respectively formed of a single crystal silicon substrate or silicon on insulator (SOI) substrate.

The valve substrate may be formed of a plastic or synthetic resin material.

A first hole connected to the inlet and a second hole connected to the outlet may be formed in the valve substrate, and the valve may be installed in at least one of the first hole and the second hole.

The valve may include: a thin film member; a first opening and closing member formed by a first cutting line to cut one part of the thin film member; and a second opening and closing member formed by a second cutting line to cut the other part of the thin film member.

The first cutting line may have a length greater than that of the second cutting line.

The first cutting line may be curved to have a first radius, and the second cutting line may be curved to have a second radius.

The first radius and the second radius may have different sizes.

According to another aspect of the present invention, there is provided a micro-pump including: a bottom substrate; a flow path forming substrate coupled to the bottom substrate and including an inlet having a fluid introduced therein and an outlet having the fluid ejected therefrom; a vibration substrate coupled to the flow path forming substrate; and a valve substrate coupled to the vibration substrate and including at least one valve controlling the fluid to be introduced and ejected.

The inlet, the outlet, and a pressure chamber connecting the inlet and the outlet to each other may be formed in the flow path forming substrate, and through holes respectively connected to the inlet and the outlet may be formed in the vibration substrate.

The micro-pump may further include: an actuator formed on a first surface of the vibration substrate and applying pressure to the pressure chamber.

The bottom substrate, the flow path forming substrate, and the vibration substrate may be respectively formed of a single crystal silicon substrate or silicon on insulator (SOI) substrate.

The valve substrate may be formed of a plastic or synthetic resin material.

A first hole connected to the inlet and a second hole connected to the outlet may be formed in the valve substrate, and the valve may be installed in at least one of the first hole and the second hole.

The valve may include: a thin film member; a first opening and closing member formed by a first cutting line to cut one part of the thin film member; and a second opening and closing member formed by a second cutting line to cut the other part of the thin film member.

The first cutting line may have a length greater than that of the second cutting line.

The first cutting line may be curved to have a first radius, and the second cutting line may be curved to have a second radius.

The first radius and the second radius may have different sizes.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE EMBODIMENTS

Hereinafter, embodiments of the present invention will be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like elements.

Figure 1:
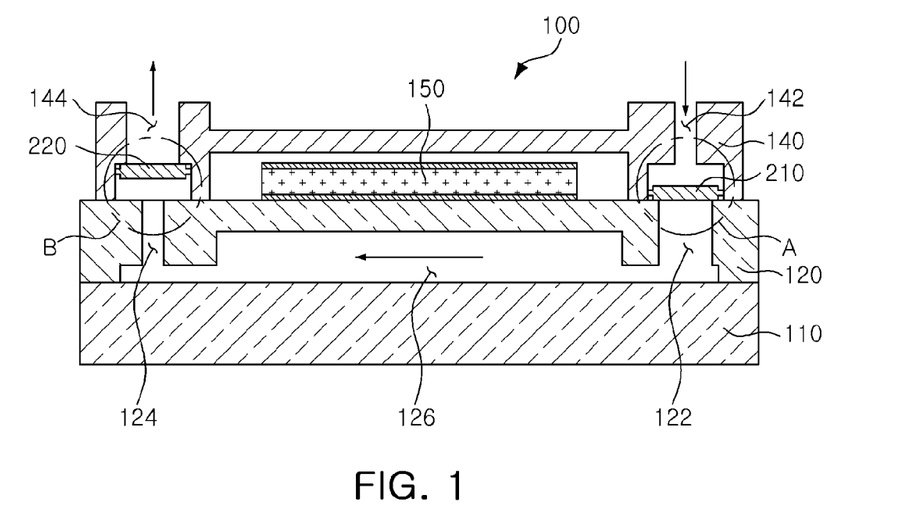
FIG. 1 is a cross-sectional view of a micro-pump according to an embodiment of the present invention.
Figure 2:
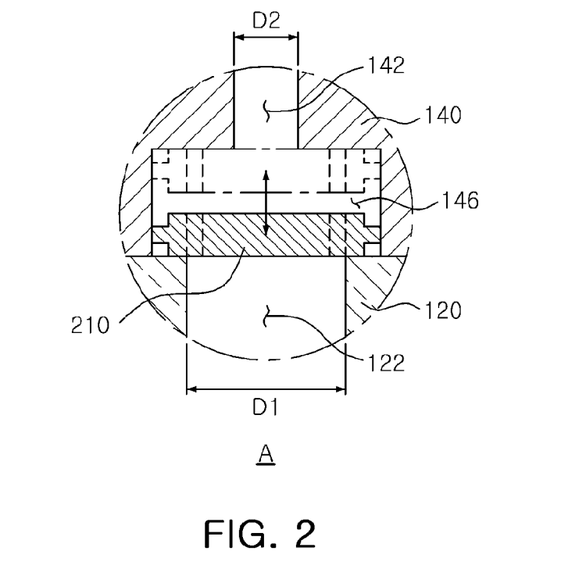
FIG. 2 is an expanded view of portion A of FIG. 1.
Figure 3:
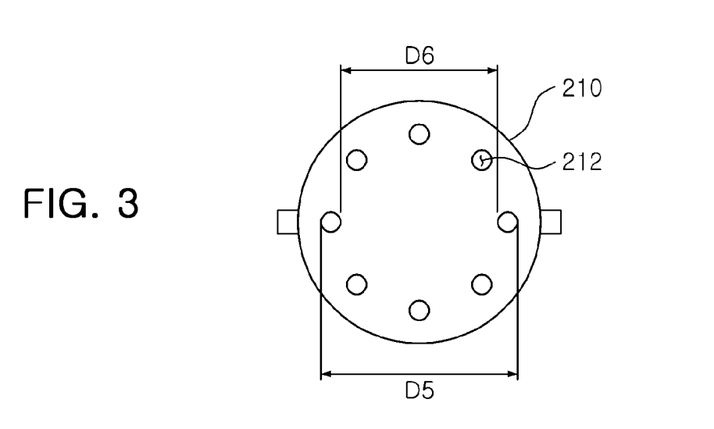
FIG. 3 is a plan view of a valve of FIG. 2.
Figure 4:
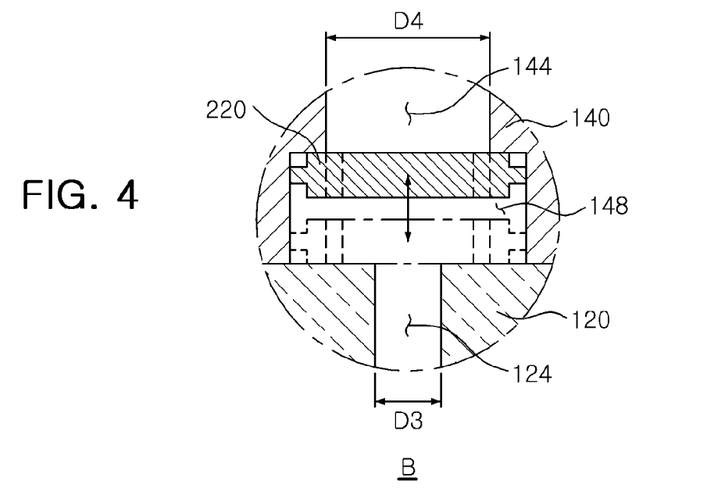
FIG. 4 is an expanded view of portion B of FIG. 1.
Figure 5:
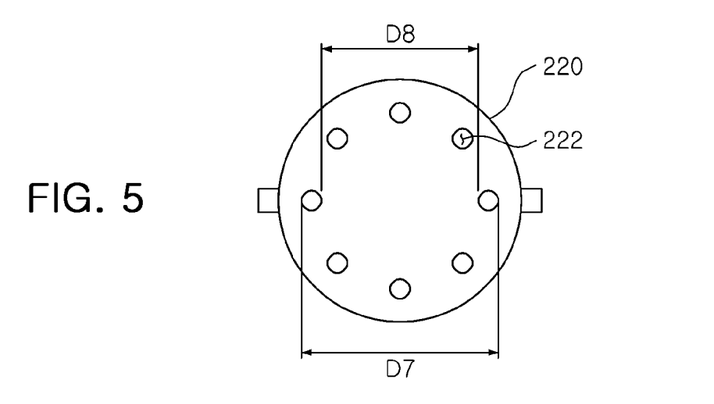
FIG. 5 is a plan view of a valve of FIG. 4.
Figure 6:
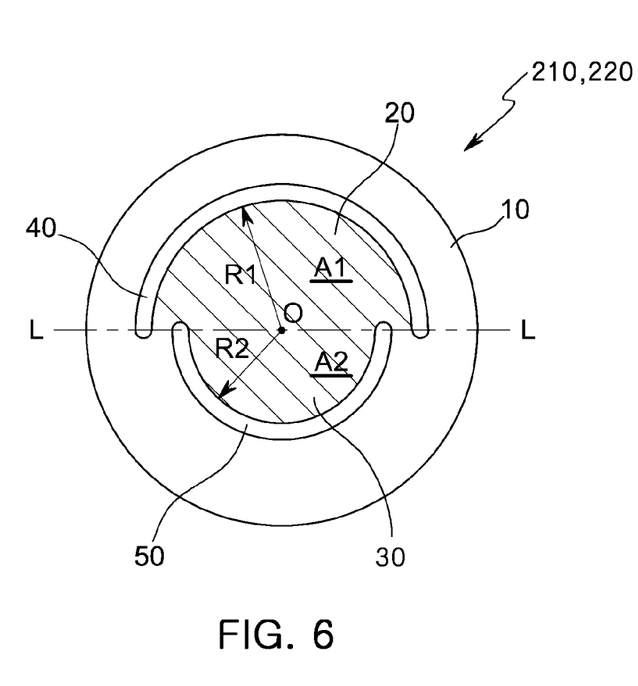
FIGS. 6 through 13 are views of modifications of a valve.
Figure 12:
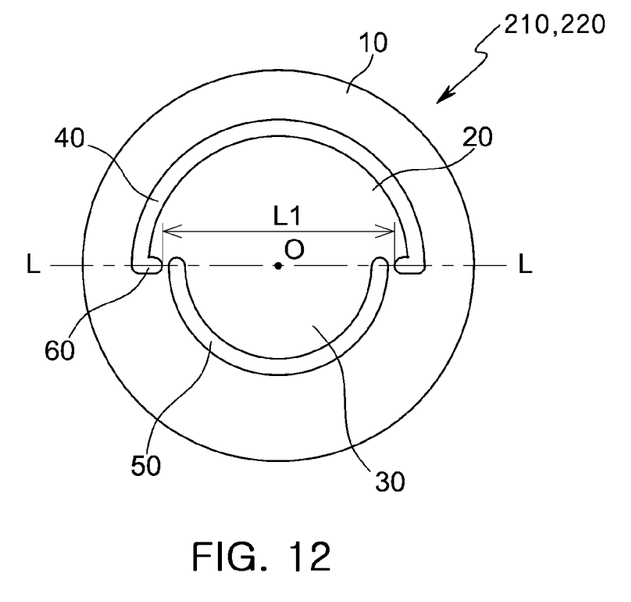
Figure 13:
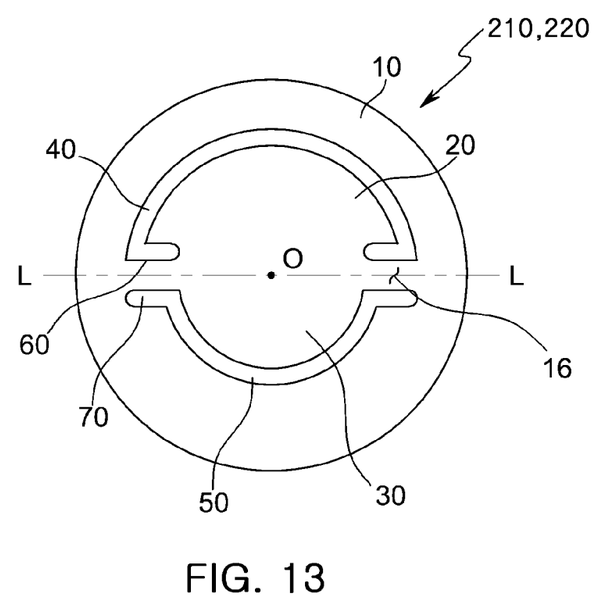
Figure 14:
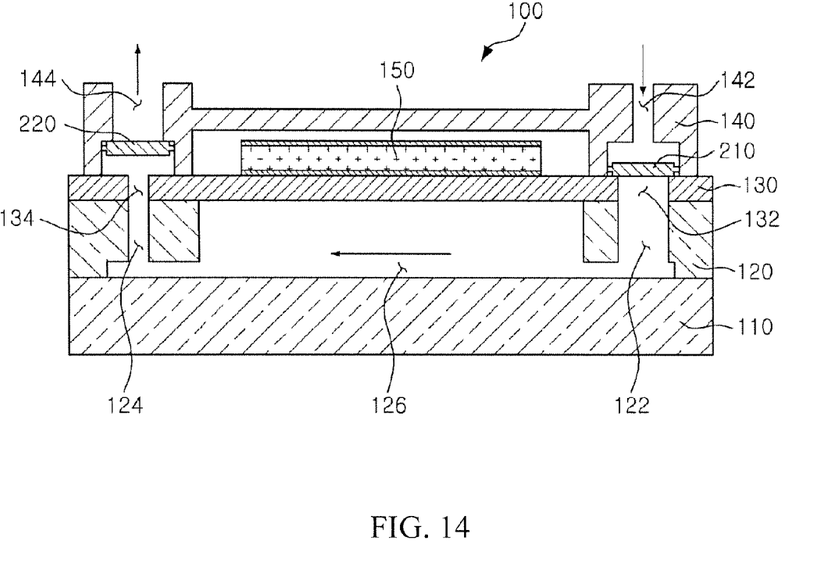
FIG. 14 is a cross-sectional view of a micro-pump according to another embodiment of the present invention.

FIG. 1 is a cross-sectional view of a micro-pump according to an embodiment of the present invention. FIG. 2 is an expanded view of portion A of FIG. 1. FIG. 3 is a plan view of a valve of FIG. 2. FIG. 4 is an expanded view of portion B of FIG. 1. FIG. 5 is a plan view of a valve of FIG. 4. FIGS. 6 through 13 are views of modifications of a valve. FIG. 14 is a cross-sectional view of a micro-pump according to another embodiment of the present invention.

A micro-pump 100 according to an embodiment of the present invention will now be described with reference to FIGS. 1 through 5.

The micro-pump 100 according to the present embodiment may include a bottom substrate 110, a flow path forming substrate 120, and a valve substrate 140. In addition, the micro-pump 100 may further include an actuator 150 if necessary. In this regard, the bottom substrate 110, the flow path forming substrate 120, and the valve substrate 140 may be sequentially stacked.

The bottom substrate 110 may form a base unit of the micro-pump 100. The bottom substrate 110 may be manufactured formed of a single crystal silicon or silicon on insulator (SOI) substrate. In this case, the bottom substrate 110 may be a stacked structure in which a silicon substrate and a plurality of insulation members are stacked.

The flow path forming substrate 120 may be a substrate in which a flow path through which a fluid (for example, a culture medium or drug) is transferred is formed. To this end, an inlet 122 and an outlet 124 may be formed in a first surface (an upper surface in FIG. 1) of the flow path forming substrate 120, and a pressure chamber 126 may be formed in a second surface (a lower surface in FIG. 1) thereof. In this regard, the pressure chamber 126 may be connected to the inlet 122 and the outlet 124, and may have a volume capable of accommodating a predetermined amount of fluid therein.

The flow path forming substrate 120 may be formed of a single crystal silicon or SOI substrate in a similar manner to the case of the bottom substrate 110. The flow path forming substrate 120 may be integrally formed with the bottom substrate 110 through a firing process.

The valve substrate 140 may be formed on one surface of the flow path forming substrate 120, and may control a movement of a fluid flowing through the flow path forming substrate 120. To this end, the valve substrate 140 may include one or more valves 210 and 220.

A first hole 142 and a second hole 144 may be formed in the valve substrate 140. In this regard, the first hole 142 may be connected to the inlet 122 of the flow path forming substrate 120, and the second hole 144 may be connected to the outlet 124 thereof.

The valves 210 and 220 may be installed in the first hole 142 and the second hole 144, respectively. In more detail, the first valve 210 may be installed in the first hole 142 and the second valve 220 may be installed in the second hole 144. Meanwhile, valves are installed in both the first hole 142 and the second hole 144 in the present embodiment; however, the valves may be installed only in a single hole if necessary.

The valve substrate 140 may be formed of a plastic or synthetic resin material. In this case, the valve substrate 140 and the valves 210 and 220 are easily processed, and thus a manufacturing cost of the valve substrate 140 may be reduced. However, if necessary, the valve substrate 140 may be formed of a silicon substrate, while the valves 210 and 220 may be formed of a plastic or synthetic resin material.

The actuator 150 may be formed on the flow path forming substrate 120. In more detail, the actuator 150 may be formed on one surface (the upper surface in FIG. 1) of the flow path forming substrate 120. The actuator 150 may be configured of a lower electrode, a piezoelectric element, and an upper electrode. In more detail, the lower electrode may be formed on an upper surface of the flow path forming substrate 120, the piezoelectric element may be formed on an upper surface of the lower electrode, and the upper electrode may be formed on an upper surface of the piezoelectric element. The above-configured actuator 150 may generate driving force as the piezoelectric element is modified by a current signal supplied through the upper electrode and the lower electrode. In this regard, the driving force of the actuator 150 is transferred to the pressure chamber 126 of the flow path forming substrate 120, which may provide a fluid flow.

Meanwhile, the micro-pump 100 may allow the fluid to flow in one direction through the valves 210 and 220. This will now be described with reference to FIGS. 2 though 5.

An entrance side (a portion indicated as A of FIG. 1) of the micro-pump 100 may be configured as shown in FIG. 2. In more detail, the inlet 122 of the flow path forming substrate 120 may have a first diameter D1, and the first hole 142 of the valve substrate 140 may have a second diameter D2. In this regard, the first diameter D1 may be greater than the second diameter D2. Meanwhile, a first space 146 in which the first valve 210 may be accommodated may be formed in a lower surface of the valve substrate 140.

The first valve 210 may be installed in the first space 146. The first valve 210 may move upwardly and downwardly in a height direction (in FIG. 2) of the first space 146 and close the first hole 142. To this end, the first valve 210 may include a plurality of ejection holes 212 as shown in FIG. 3. In this regard, a diameter D6 of a circle with which the plurality of ejection holes 212 come into internal contact may be greater than the second diameter D2 of the first hole 142, and a diameter D5 of a circle with which the plurality of ejection holes 212 come into external contact may be greater than the second diameter D2 of the first hole 142 but may be smaller than the first diameter D1 of the inlet 122.

In a case in which a fluid moves from the first hole 142 to the inlet 122 in the entrance side of the above-configured micro-pump 100, the ejection holes 212 are opened as the first valve 210 moves downwardly, and thus the movement of the fluid may be facilitated. However, in a case in which fluid moves from the inlet 122 to the first hole 142, the first hole 142 may be closed as the first valve 210 moves upwardly, and thus the movement of the fluid may be blocked.

An exit side (a portion indicated as B of FIG. 1) of the micro-pump 100 may be configured as shown in FIG. 4.

In more detail, the outlet 124 of the flow path forming substrate 120 may have a third diameter D3, and the second hole 144 of the valve substrate 140 may have a fourth diameter D4. In this regard, the third diameter D3 may be smaller than the fourth diameter D4. Meanwhile, a second space 148 in which the second valve 220 may be accommodated may be formed in the lower surface of the valve substrate 140.

The second valve 220 may be installed in the second space 148. The second valve 220 may move upwardly and downwardly in a height direction (in FIG. 4) of the second space 148 and close the outlet 124. To this end, the second valve 220 may include a plurality of ejection holes 222 as shown in FIG. 5. In this regard, a diameter D8 of a circle with which the plurality of ejection holes 222 come into internal contact may be greater than the third diameter D3 of the outlet 124, and a diameter D7 of a circle with which the plurality of ejection holes 222 come into external contact may be smaller than the fourth diameter D4 of the second hole 144.

In a case in which fluid moves from the outlet 124 to the second hole 144 in the exist side of the above-configured micro-pump 100, the ejection holes 222 are opened as the second valve 220 moves upwardly, and thus the movement of the fluid may be allowed. However, in a case in which the fluid moves from the second hole 144 to the outlet 124, the ejection holes 222 are closed as the second valve 220 moves downwardly, and thus the movement of the fluid may be blocked.

A direction of fluid movement is controlled by the valves 210 and 220 in the above-configured micro-pump 100, and thus, advantageously, a small amount of fluid may be uniformly moved. In addition, in the micro-pump 100, only the valve substrate 140 in which the valves 210 and 220 are formed may be separately manufactured, thereby simplifying a manufacturing process of the micro-pump 100 and reducing a manufacturing cost of the micro-pump 100.

Modifications of a valve will now be described with reference to FIGS. 6 through 13. A first example of the valves 210 and 220 will now be described with reference to FIGS. 6 through 8.

The first example of the valves 210 and 220 may include a thin film member 10, a first opening and closing member 20, and a second opening and closing member 30. In this regard, the thin film member 10, the first opening and closing member 20, and the second opening and closing member 30 may be integrally formed. In more detail, the first opening and closing member 20 and the second opening and closing member 30 may be formed by processing the thin film member 10.

The thin film member 10 may be a membrane having a circular cross-section. However, a cross-sectional shape of the thin film member 10 is not limited to a circular shape. For example, the thin film member 10 may have a polygonal cross-section, including a rectangular cross-section.

The thin film member 10 may be formed of an elastic material. When further explained, the thin film member 10 may be formed of a material which may be bent or deformed when a predetermined degree of force is applied thereto. For example, the thin film member 10 may be formed of a material such as plastic or rubber, or a synthetic resin or metal. However, the material of the thin film member 10 is not limited to the aforementioned materials and the thin film member 10 may be manufactured by any material having a predetermined degree of elastic force.

Figure 7:
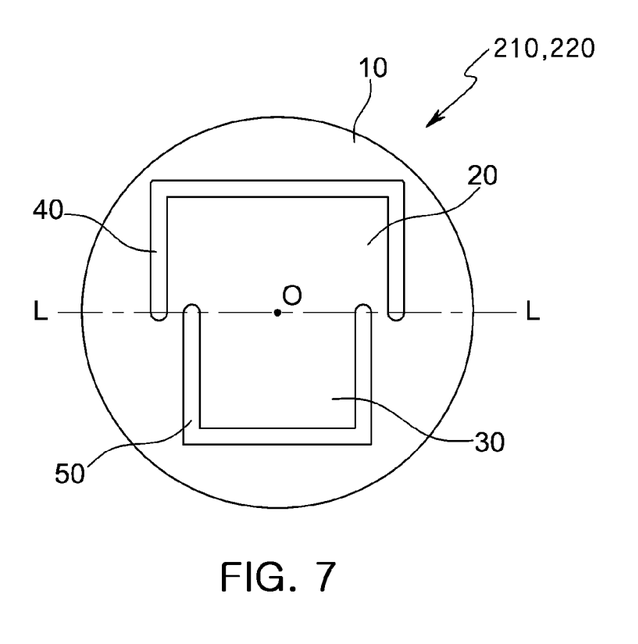
Figure 8:
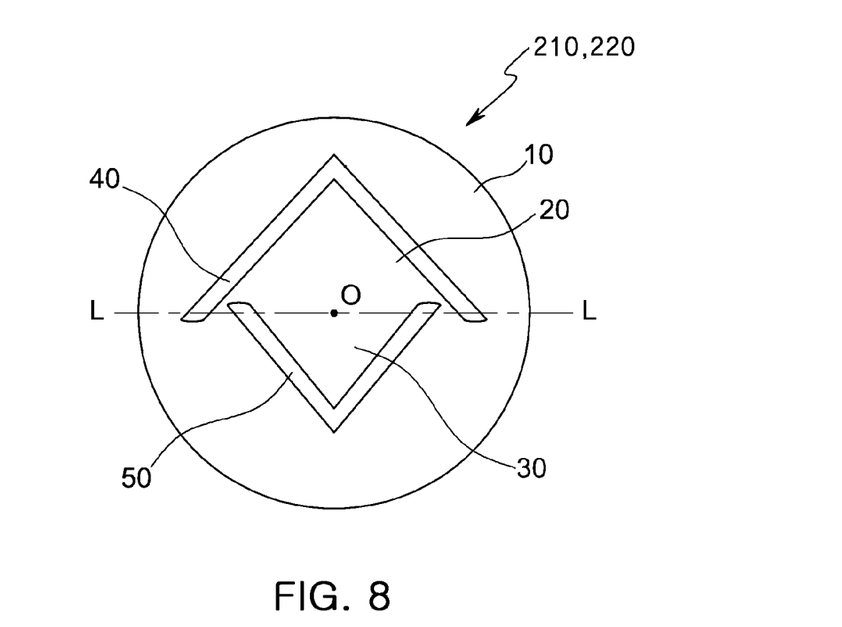

The first opening and closing member 20 may be formed in one part of the thin film member 10. When further explained, the first opening and closing member 20 may be formed in an upper part of the thin film member 10 by a first cutting line 40. Herein, the first cutting line 40 may be curved to have a first radius R1. In this case, the first opening and closing member 20 may have a substantially semicircular shape. However, the shapes of the first opening and closing member 20 and the first cutting line 40 are not limited to shapes illustrated in FIG. 6. For example, the first opening and closing member 20 may have a rectangular or triangular shape as illustrated in FIGS. 7 and 8, and the first cutting line 40 may be formed as a plurality of straight lines rather than as a curve.

The first opening and closing member 20 may be opened and closed based on a horizontal line segment L-L. For example, the first opening and closing member 20 may rotate about the horizontal line segment L-L as a central axis. Herein, a rotational direction of the first opening and closing member 20 may depend on locations in which the valves 210 and 220 are installed.

The second opening and closing member 30 may be formed in the other part of the thin film member 10. When further explained, the second opening and closing member 30 may be formed in a lower part of the thin film member 10 by a second cutting line 50. Herein, the second cutting line 50 may be curved to have a second radius R2. In this case, the second opening and closing member 30 may have a substantially semicircular shape. However, the shapes of the second opening and closing member 30 and the second cutting line 50 are not limited to shapes illustrated in FIG. 6. For example, the second opening and closing member 30 may have the rectangular or triangular shape as illustrated in FIGS. 7 and 8, and the second cutting line 50 may be formed as a plurality of straight lines rather than as a curve.

The second opening and closing member 30 may be opened and closed based on the horizontal line segment L-L in a similar manner to the case of the first opening and closing member 20. For example, the second opening and closing member 30 may rotate about the horizontal line segment L-L as a central axis. Herein, a rotational direction of the second opening and closing member 30 may be opposite to that of the first opening and closing member 20. For example, when the first opening and closing member 20 is opened forwardly, the second opening and closing member 30 is opened backwardly while when the first opening and closing member 20 is opened backwardly, the second opening and closing member 30 is opened forwardly.

The first opening and closing member 20 and the second opening and closing member 30 may respectively have predetermined areas. When further explained, the first opening and closing member 20 may have a first area A1 and the second opening and closing member 30 may have a second area A2. Herein, the first area A1 of the first opening and closing member 20 may be larger than the second area A2 of the second opening and closing member 30. To this end, the length of the first cutting line 40 may be greater than that of the second cutting line 50. Alternatively, the first radius R1 of the first cutting line 40 may be larger than the second radius R2 of the second cutting line 50.

As such, when the areas of the first opening and closing member 20 and the second opening and closing member 30 are different from each other, the magnitudes of force acting on the first opening and closing member 20 and the second opening and closing member 30 may be different from each other, which may cause the force to be concentrated on the first opening and closing member 20, such that the rotation (that is, opening) of the first opening and closing member 20 may be induced. Herein, since the first opening and closing member 20 and the second opening and closing member 30 are integrally formed to move together, the rotation of the first opening and closing member 20 may also induce the rotation of the second opening and closing member 30. Accordingly, according to the embodiment, the first opening and closing member 20 and the second opening and closing member 30 are opened or closed simultaneously to control the flow of a fluid.

Meanwhile, a difference in area between the first opening and closing member 20 and the second opening and closing member 30 may depend on a magnitude of the elastic force of the thin film member 10. For example, when the elastic force of the thin film member 10 is high, the difference in area between the first opening and closing member 20 and the second opening and closing member 30 may be increased and when the elastic force of the thin film member 10 is relatively low, the difference in area between the first opening and closing member 20 and the second opening and closing member 30 may be decreased. The reason for this is that the opening and closing members 20 and 30 may only rotate when force caused by the difference in area between the first opening and closing member 20 and the second opening and closing member 30 is larger than the elastic force of the thin film member 10.

For reference, in the embodiment, both ends of the first cutting line 40 and both ends of the second cutting line 50 may be positioned on the horizontal line segment L-L intersecting a center point O. In this case, since rotation reference points of the first opening and closing member 20 and the second opening and closing member 30 are positioned on the same line, the first opening and closing member 20 and the second opening and closing member 30 may smoothly rotate simultaneously.

The above-configured valves 210 and 220 form the sizes of the first opening and closing member 20 and the second opening and closing member 30 are set to be different from each other, and as a result, opening conditions of the opening and closing members 20 and 30 may be set. Therefore, even in a pipe through which a small amount of fluid moves, the flow of the fluid may be effectively controlled by controlling the difference in area between the first opening and closing member 20 and the second opening and closing member 30.

Figure 9:
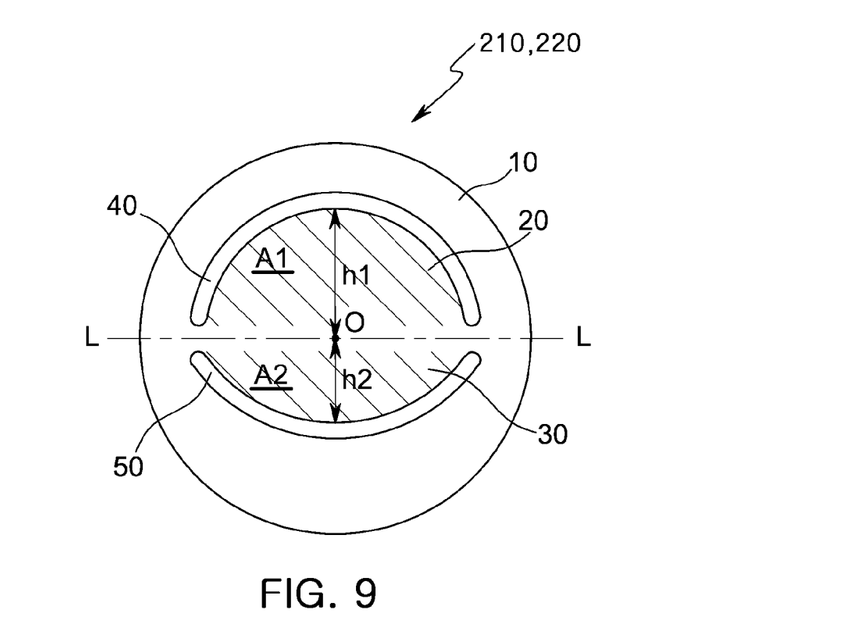

A second example of the valves 210 and 220 will now be described with reference to FIGS. 9 through 11.

The second example of the valves 210 and 220 may be distinguished from that of the first example in that heights from the center point O of the thin film member 10 to apexes of the cutting lines 40 and 50 are different from each other. That is, a height h1 from the center point O to the apex of the first cutting line 40 may be different from a height h2 from the center point O to the second cutting line 50.

This structure may naturally induce the difference in area between the first opening and closing member 20 and the second opening and closing member 30. Moreover, in this structure, since a portion in which the both ends of the first cutting line 40 and the second cutting line 50 are separated from each other serves as a rotational shaft, the first opening and closing member 20 and the second opening and closing member 30 may smoothly rotate.

Figure 10:
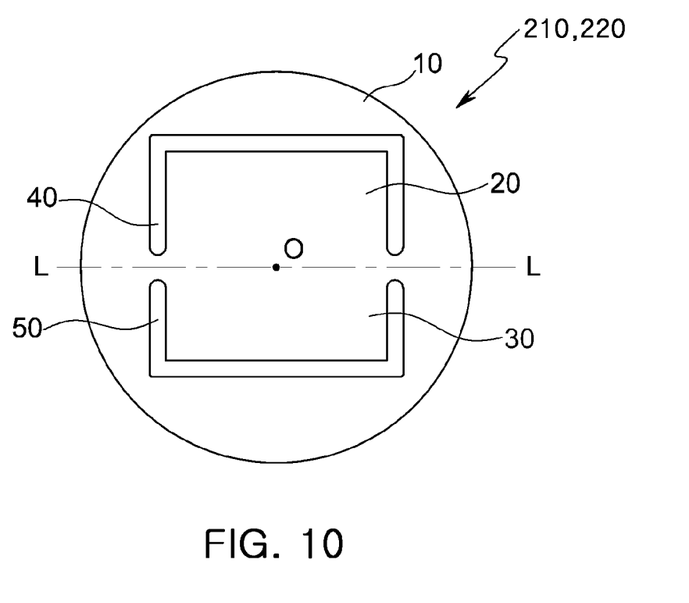
Figure 11:
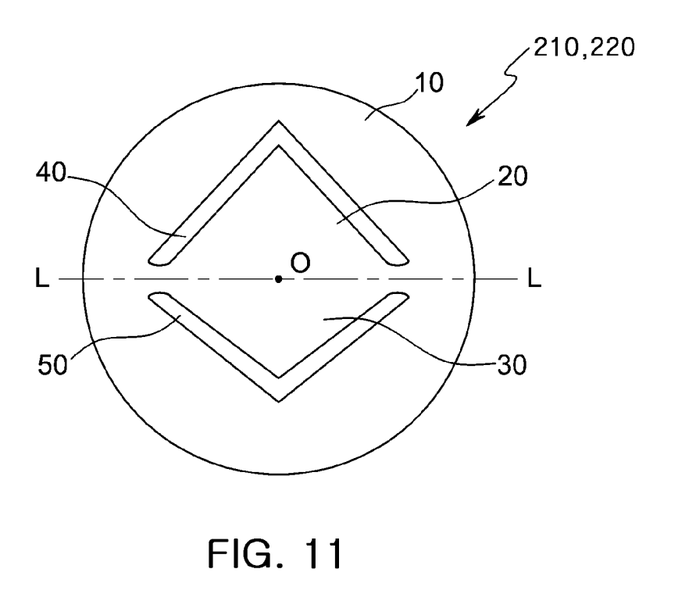

Meanwhile, the shapes of the first opening and closing member 20 and the second opening and closing member 30 may be deformed as illustrated in FIGS. 10 and 11, and to this end, the first cutting line 40 and the second cutting line 50 may be formed by the plurality of straight lines.

A third example and a fourth example of the valves 210 and 220 will now be described with reference to FIGS. 12 and 13.

The third example of the valves 210 and 220 may be distinguished from those of the foregoing examples in that the valves 210 and 220 include third cutting lines 60 and fourth cutting lines 70.

The third example of the valves 210 and 220 may further include the third cutting lines 60. The third cutting lines 60 may extend inwardly in a direction toward the center point O from both ends of the first cutting line 40. The third cutting lines 60 are not connected to the second cutting line 50, but may be positioned on the same line as both ends of the second cutting line 50.

In the valves 210 and 220 formed as above, since a connection length L1 between the thin film member 10 and the first opening and closing member 20 is shortened by the third cutting lines 60, the first opening and closing member 20 may be more smoothly moved.

The fourth example of the valves 210 and 220 may further include the third cutting lines 60 and the fourth cutting lines 70. The third cutting lines 60 may extend inwardly from both ends of the first cutting line 40 and the fourth cutting lines 70 may extend outwardly from both ends of the second cutting line 50. Herein, since both ends of the first cutting line 40 and both ends of the second cutting line 50 are formed to be separated from each other by a predetermined interval, the third cutting lines 60 and the fourth cutting lines 70 may not be connected to each other.

In the valves 210 and 220 formed as above, since a shaft 16, a rotation reference of the first opening and closing member 20 and the second opening and closing member 30 is formed by the third cutting lines 60 and the fourth cutting lines 70, the first opening and closing member 20 and the second opening and closing member 30 may smoothly rotate.

The micro-pump 100 according to another embodiment of the present invention will now be described with reference to FIG. 14. For reference, the same elements between another embodiment and the above-described embodiments denote the same reference numerals, and detailed descriptions thereof will be omitted here.

The micro-pump 100 according to another embodiment may be distinguished from the above-described embodiment in terms of the flow path forming substrate 120 and a vibration substrate 130.

The flow path forming substrate 120 may include the inlet 122, the outlet 124, and the pressure chamber 126 in like manner to the above-described embodiment. However, the pressure chamber 126 according to the embodiment may be completely open in a vertical direction, unlike the above-described embodiment. The pressure chamber 126 having the above shape may be easily formed by an etching process (in particular, a wet etching process). A size and volume of the pressure chamber 126 may be easily changed by adjusting a thickness of the flow path forming substrate 120.

The vibration substrate 130 may be coupled to the flow path forming substrate 120. The vibration substrate 130 may be formed of a single crystal silicon or SOI substrate. Through holes 132 and 134 may be formed in the vibration substrate 130. In this regard, the first through hole 132 may connect the inlet 122 and the first hole 142, and the second through hole 134 may connect the outlet 124 and the second hole 144.

In the above-configured micro-pump 100, the flow path forming substrate 120 may be easily manufactured through an etching process. In addition, the vibration substrate 130 is separately manufactured, such that the slimness of the vibration substrate 130 may be facilitated, thereby reducing current consumption required for driving the actuator 150.

As set forth above, according to embodiments of the invention, a fluid including a fine material, for example, a micromaterial can be effectively transferred.

In addition, according to embodiments of the invention, a micro-pump can separately manufacture a valve substrate, thereby simplifying a manufacturing process of the micro-pump and reducing a manufacturing processing cost.

While the present invention has been shown and described in connection with the embodiments, it will be apparent to those skilled in the art that modifications and variations can be made without departing from the spirit and scope of the invention as defined by the appended claims.

What is claimed is:

1. A micro-pump comprising:
   a bottom substrate;
   a flow path forming substrate coupled to the bottom substrate and including an inlet having a fluid introduced therein and an outlet having the fluid ejected therefrom; and
   a valve substrate coupled to the flow path forming substrate and including at least one valve controlling the fluid to be introduced and ejected,
      wherein a first hole connected to the inlet and a second hole connected to the outlet are formed in the valve substrate; and
      the valve is installed in at least one of the first hole and the second hole,
      wherein the valve includes:
      a thin film member;
      a first opening and closing member formed by a first cutting line to cut one part of the thin film member; and
      a second opening and closing member formed by a second cutting line to cut the other part of the thin film member;
      wherein the thin film member is formed of an elastic material; and
      areas of the first opening and closing member and the second opening and closing member are different from each other.

2. The micro-pump according to claim 1, wherein the inlet and outlet are formed in a first surface of the flow path forming substrate, and
   a pressure chamber connecting the inlet and the outlet is formed in a second surface of the flow path forming substrate.

3. The micro-pump according to claim 2, further comprising an actuator formed on the first surface of the flow path forming substrate and applying pressure to the pressure chamber.

4. The micro-pump according to claim 1, wherein the bottom substrate and the flow path forming substrate are respectively formed of a single crystal silicon substrate or silicon on insulator (SOI) substrate.

5. The micro-pump according to claim 1, wherein the valve substrate is formed of a plastic or synthetic resin material.

6. The micro-pump according to claim 1, wherein the first cutting line has a length greater than that of the second cutting line.

7. The micro-pump according to claim 1, wherein the first cutting line is curved to have a first radius, and
   the second cutting line is curved to have a second radius.

8. The micro-pump according to claim 7, wherein the first radius and the second radius have different sizes.

9. A micro-pump comprising:
   a bottom substrate;
   a flow path forming substrate coupled to the bottom substrate and including an inlet having a fluid introduced therein and an outlet having the fluid ejected therefrom;
   a vibration substrate coupled to the flow path forming substrate; and
   a valve substrate coupled to the vibration substrate and including at least one valve controlling the fluid to be introduced and ejected
   wherein a first hole connected to the inlet and a second hole connected to the outlet are formed in the valve substrate; and
   the valve is installed in at least one of the first hole and the second hole,
      wherein the valve includes:
      a thin film member;
      a first opening and closing member formed by a first cutting line to cut one part of the thin film member; and
      a second opening and closing member formed by a second cutting line to cut the other part of the thin film member;
      wherein the thin film member is formed of an elastic material, and
      areas of the first opening and closing member and the second opening and closing member are different from each other.

10. The micro-pump according to claim 9, wherein the inlet, the outlet, and a pressure chamber connecting the inlet and the outlet to each other are formed in the flow path forming substrate, and
    through holes respectively connected to the inlet and the outlet are formed in the vibration substrate.

11. The micro-pump according to claim 10, further comprising an actuator formed on a first surface of the vibration substrate and applying pressure to the pressure chamber.

12. The micro-pump according to claim 9, wherein the bottom substrate, the flow path forming substrate, and the vibration substrate are respectively formed of a single crystal silicon substrate or silicon on insulator (SOI) substrate.

13. The micro-pump according to claim 9, wherein the valve substrate is formed of a plastic or synthetic resin material.

14. The micro-pump according to claim 9, wherein the first cutting line has a length greater than that of the second cutting line.

15. The micro-pump according to claim 9, wherein the first cutting line is curved to have a first radius, and
    the second cutting line is curved to have a second radius.

16. The micro-pump according to claim 15, wherein the first radius and the second radius have different sizes.

* * * * *